United States Patent [19]

Parks

[11] 4,298,006
[45] Nov. 3, 1981

[54] SYSTEMIC HYPERTHERMIA WITH IMPROVED TEMPERATURE SENSING APPARATUS AND METHOD

[75] Inventor: Leon C. Parks, Brandon, Miss.

[73] Assignee: Research Against Cancer, Inc., Jackson, Miss.

[21] Appl. No.: 145,053

[22] Filed: Apr. 30, 1980

[51] Int. Cl.³ .............................................. A61F 7/00
[52] U.S. Cl. .................... 128/399; 128/1 R; 128/736
[58] Field of Search ............... 128/401, 399, 400, 402, 128/214 R, 214 A, 347, 348, 303.1, 736, 1 R

[56] References Cited

U.S. PATENT DOCUMENTS

| | | | |
|---|---|---|---|
| 958,854 | 5/1910 | Bunn | 128/347 |
| 3,064,649 | 11/1962 | Fuson | 128/214 |
| 3,982,535 | 9/1976 | Bahrton | 128/DIG. 3 |
| 3,998,222 | 12/1976 | Shihata | 128/214 R |

FOREIGN PATENT DOCUMENTS

| | | | |
|---|---|---|---|
| 1566620 | 10/1970 | Fed. Rep. of Germany | 128/399 |
| 1140895 | 8/1957 | France | 128/399 |
| 1521064 | 4/1968 | France | 128/399 |

OTHER PUBLICATIONS

Hyperthermia is the Treatment of the Cancer Patient, Cancer 37:2075-2983, 1976.
Introduction of Controlled Hyperthermia in Treatment of Cancer, Henderson et al., Lancet 1:1275.
Proceedings of the International Symp. on Cancer Therapy by Hyperthermia and Radiation, Apr. 28-30, 1975.
Effect of Hyperthermia on the Radiosensitivity of Normal and Malignant Cells in Mice, Hofer et al., Cancer 38:279, 1976.
Total Body Hyperthermia and Preliminary Results in Human Neoplasms, Larkin et al., Sur. Forum 27:121, 1976.
Exploiting Heat Sensitivity in Leukemic Cells, Wheldon, Lancet 1:1363, 1976.

*Primary Examiner*—Stephen C. Pellegrino
*Attorney, Agent, or Firm*—Cushman, Darby & Cushman

[57] ABSTRACT

An improvement in a method of treating cancer by systemic hyperthermia which comprises measuring the patient's core body temperature in the bladder and controlling the inducement of systemic hyperthermia in accordance with the bladder temperature measured.

4 Claims, 3 Drawing Figures

SYSTEMIC HYPERTHERMIA WITH IMPROVED TEMPERATURE SENSING APPARATUS AND METHOD

BACKGROUND AND SUMMARY OF THE INVENTION

This invention relates to the treatment of cancer by hyperthermia and more particularly to improvements in the control of whole body or systemic hyperthermia for purposes of retarding the growth of cancel cells.

In my application, Ser. No. 802,033, filed May 31, 1977, now U.S. Pat. No. 4,181,132, there is disclosed a method of effecting whole body or systemic hyperthermia within an individual for anticancer purposes. The method as disclosed involves the establishment and utilization of a sterile extracorporeal flow path for blood having an inlet, an outlet and a temperature control zone therebetween. The extracorporeal flow path is connected with the patient by establishing communication of the inlet of the extracorporeal flow path with the patient's blood stream so that the blood can be withdrawn and supplied to the extracorporeal flow path without adversely affecting the blood circulation in the areas from which the blood is withdrawn. The extracorporeal flow path is also connected with the patient by establishing communication of the outlet of the extracorporeal flow path with the patient's blood stream so that blood flowing from the extracorporeal flow path is returned to the blood stream in such a way as to be distributed systemically. The blood withdrawn from the patient's blood stream is pumped along the extracorporeal flow path through the temperature control zone at a controlled rate of at least approximately one liter per minute for return to the patient's blood stream. The temperature of the blood flowing along the extracorporeal flow path through the temperature control zone is controlled in accordance with the patient's core body temperature. The apparatus for sensing the patient's core temperature disclosed in my prior patent is a rectal probe or an esophageal probe.

Experimental practice of the method as disclosed in my prior patent has indicated that it is highly desirable in the efficacy of the treatment to be able to control the body temperature within 0.1° to 0.2° C. To secure this control there are two aspects which must be present. First, the method utilized to induce the systemic heat must provide such accuracy; and second, the method of sensing the systemic body temperature must likewise be capable of such accuracy. Clearly, to secure maximum effect it is desirable to provide the highest possible heat which is within the tolerance of the patient. This efficacy cannot be achieved by a system capable of inducing such heat if temperature sensing means is not available to determine within the same degree of accuracy just what temperature is being induced. Likewise, the greatest efficacy is not achieved if sufficient accuracy is provided in the temperature sensing of the patient but the means for inducing the systemic temperature is not sufficiently accurate.

Experimental use of the procedures disclosed in my prior patent clearly indicate that the desired accuracy can be obtained by the utilization of an extracorporeal heating circuit in the manner disclosed therein. However, the full efficacy of the procedure has not been consistently realized by the sensing of the patient's body core temperature at the traditional locales of the rectum or esophagus or even the possible third traditional location of the tympanic membrane. For example, when utilizing an esophageal probe there are found to exist three temperature zones depending upon the particular location of the temperature probe in the esophagus rendering the results different depending upon the particular location where use actually takes place. First, where the temperature probe has a position adjacent the right main bronchus, the temperature tends to depend too much on the temperature of the air with which the patient is ventilated. Where the esophageal probe temperature element has a position adjacent the left atrium of the heart, the humidity of the air with which the patient is ventilated can cause somewhat artificially deviant temperature readouts. For example, where the air is too dry, the tendency was to obtain temperature readouts which are slightly too cool. On the other hand, where the air humidity is wet, the temperature sensed appeared to be artifically elevated somewhat. These two locations compared with the remaining locations in the esophagus indicate a difference in the temperature sensed to be between ±0.2 to 0.6° C. in utilizing an esophageal probe.

Likewise various inaccuracies could be introduced by the utilization of a rectal probe. For example, the position of the probe could be altered by the normal peristalsis. Moreover, the tip can be encased by stool so as to present an insulation resulting in lower artificial temperature readings. The other traditional locale of the tympanic membrane presents inaccuracies because of the tendency of the accuracy of the readout to be dependent upon actual contact with the very delicate tympanic membrane. Thus, with this location there is a tendency toward light and intermittent contact resulting in artificially lower temperature readings.

It is an object of the present invention to obviate the inaccuracies noted above in sensing patient core body temperature in the traditional locales by utilizing instead a temperature readout of the bladder of the patient. It has been found that a temperature readout in the bladder achieves a consistency of accuracy which is superior to that provided by sensing temperature in the usual three traditional locales because of its central visceral location and also because urine draining from a core organ, the kidney, constantly flows into the bladder. These two factors insure that a thermistor tipped catheter placed into the bladder will enable accurate determination of true body core temperature. In addition urinary catheters are relatively sanitary and comfortable and may readily be retained in position. Inasmuch as a bladder catheter will always be placed in a seriously ill patient, the incorporation of a temperature sensing device such as a thermistor or thermocouple in its tip not only poses no additional discomfort to the patient, but relieves him of the necessity of having another probe inserted into still another orifice.

It is recognized that it has been proposed to provide a thermistor in the tip of a conventional bladder catheter. Such a proposal is contained in an IBM technical disclosure bulletin entitled "Central Body Temperature Apparatus" by E. R. Ellinwood and G. C. Rastelli, Vol. 11, No. 11, dated April of 1969. This disclosure, however, does not suggest the utilization of such a device in systemic hyperthermia nor has the proposed device, to applicant's knowledge, ever been actually produced and utilized in any medical procedure, much less whole body hyperthermia.

It will be understood that whole body or systemic hyperthermia has been induced by others by means other than an extracorporeal heat circuit as described in my prior patent. For example, others have proposed the utilization of hot wax baths or externally applied hot water controlled blankets. As far as applicant is aware none of these methods of inducing systemic hyperthermia has heretofore been controlled by sensing the core body temperature by a bladder temperature sensing probe. Indeed, it may be that the accuracies of induced core body temperature which can be achieved by these procedures is equal to the temperature sensing accuracies that can be achieved by sensing temperature at one or more of the traditional locations. Thus, while the improvements relating to the control of systemic hyperthermia by sensing bladder temperature of the present invention has particular efficacy when utilized to control systemic hyperthermia induced by an extracorporeal blood circuit, such improvement would have equal applicability to systemic hyperthermia induced by any other method capable of achieving accuracies similar to that achieved by the extracorporeal blood circuit method.

Another object of the present invention is the provision of improvements in the apparatus used in inducing hyperthermia through an extracorporeal circuit, such improvements embodying the utilization of a temperature sensing probe in the tip of a bladder catheter.

These and other objects of the present invention will become more apparent during the course of the following detailed description and appended claims.

DETAILED DESCRIPTION OF THE PREFERRED EMBODIMENT

The invention may best be understood with reference to the accompanying drawings, wherein an illustrative embodiment is shown.

Referring now more particularly to the drawings, there is shown therein a preferred apparatus 10 to which the principles of the present invention are applied for practicing the improved method of the present invention. Except for the improvements, the apparatus 10 is similar to the apparatus disclosed in my prior patent, hence, the disclosure of the patent is hereby incorporated by reference into the present specification.

As set forth in my prior patent, the apparatus 10 includes sterile tubing, generally indicated at 12, which defines an extracorporeal blood flow path. A pump mechanism preferably in the form of a peristaltic roller pump, generally indicated at 14, is provided for pumping blood along the extracorporeal flow path at a controlled rate from the inlet tubing end to the outlet tubing end. In addition, there is provided a temperature control zone preferably in the form of a heat exchanger assembly 16 through which the blood flowing along the extracorporeal flow path has its temperature controlled, preferably both by heating and cooling, through a control device, generally indicated at 18, for the liquid circuit of the heat exchanger assembly 16. Finally, the apparatus 10 includes means, generally indicated at 20, for communicating the inlet end of the tubing 12 defining the extracorporeal flow path with the bloodstream of a patient and the outlet end of the tubing 12 defining the extracorporeal flow path with the bloodstream of the patient, so that the returning blood is systemically distributed without adversely affecting the blood depleted areas from which the blood is withdrawn.

The tubing 12 may be formed of any suitable plastic material, as, for examle, vinyl polymer (e.g. Tygon ®), polytetraflouroethylene (e.g. Teflon ®), or other plastic materials having known uses in medical applications (e.g. Silastic ®). An exemplary tubing size is ¼" i.d., with a convenient length being from 3–5'. The pump assembly 16, as previously indicated, preferably embodies a peristaltic roller type pump driven by a variable speed electric motor. A peristaltic pump is preferred because it can utilize the replaceable sterile tubing 12 for blood contact and does not provide pump parts which must be maintained in a sterile condition. An exemplary pump is manufactured by Sarns, having a 1–2 liter per minute capacity.

A preferred embodiment of the heat exchanger assembly 16 is available commercially under the tradename Travenol Mini-Prime, 5MO 337, which has a 57 cc capacity and rated flow of 1–3 liters per minute. See also U.S. Pat. No. 3,640,340, the disclosure of which is hereby incorporated by reference into the present specification. In addition, the heat exchanger disclosed in commonly assigned U.S. Patent Application Ser. No. 79,955 filed Sept. 28, 1979 may also be used and hence this disclosure is also hereby incorporated by reference into the present specification.

Figure 2:
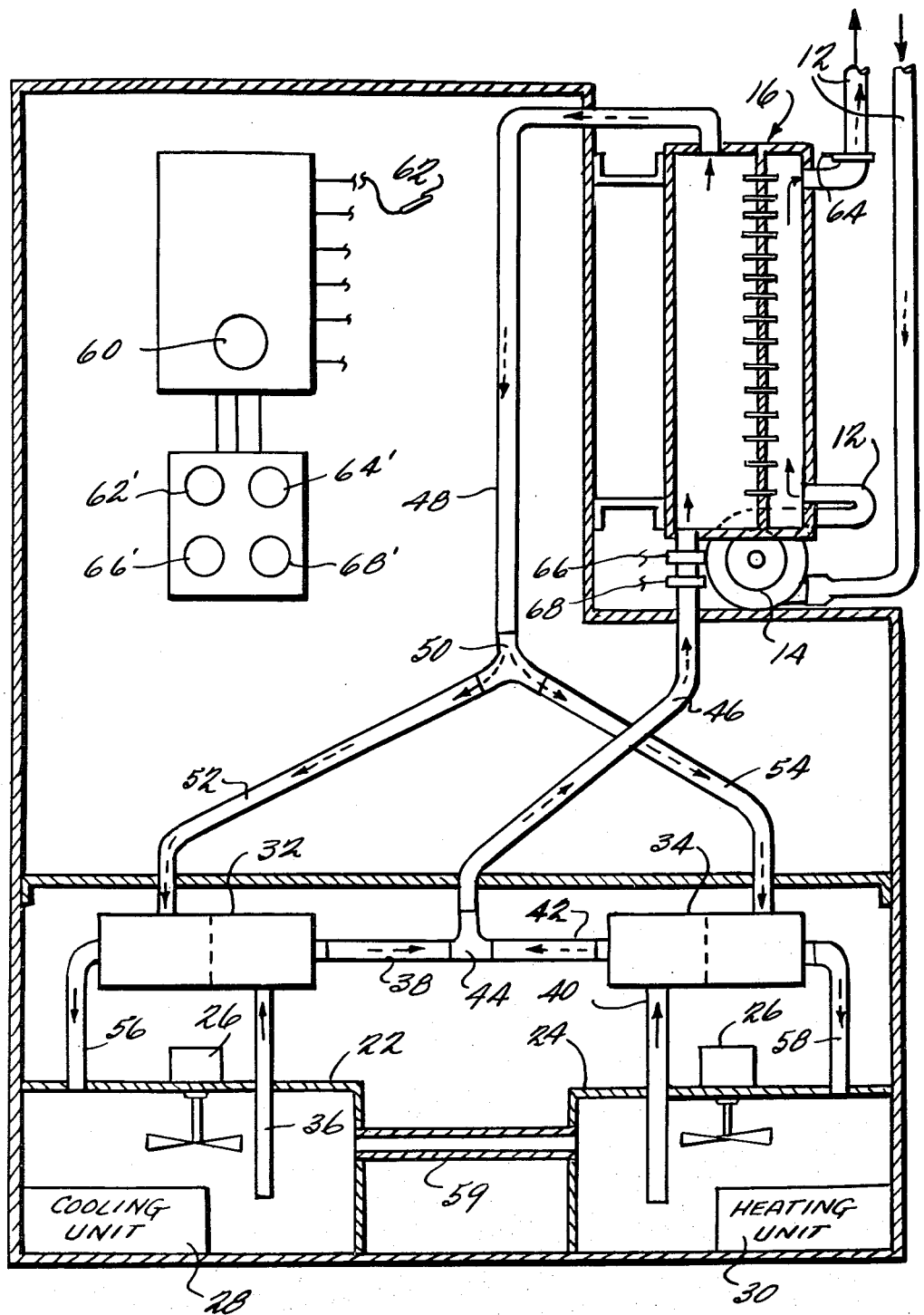
FIG. 2 is an enlarged vertical sectional view taken along the line 2—2 of FIG. 1.

With reference to FIG. 2, the control device 18 is made up of individually known components. As shown, there is provided a cooled liquid reservoir 22 and a heated liquid reservoir 24 each containing a body of liquid. While any liquid may be utilized a preferred embodiment is water. Each reservoir is provided with a stirring or agitating means 26 for purposes of mixing the liquid contained therein so as to render the temperature thereof more uniform throughout. The cool liquid reservoir 22 is provided with a cooling unit, schematically indicated at 28, while the heated liquid reservoir 24 is provided with a heating unit 30. A liquid circulating system is provided in cooperating relation between the cooled liquid reservoir 22 and heated liquid reservoir 24 and the liquid side of the heat exchanger 16. Such circulating system includes the utilization of two pump assemblies, schematically indicated in the drawings at 32 and 34.

As shown in FIG. 2, the pump assembly 32 is associated with the cooling liquid reservoir 22 and includes an inlet or suction pipe 36 extending from the reservoir 22 to one side of the pump 32 and an outlet pipe 38 extending therefrom. Similarly, an inlet pipe 40 extends from the heated liquid reservoir 24 to one side of the pump 34 which side has an outlet pipe 42 extending therefrom. Outlet pipes 38 and 42 are interconnected by a T-connector 44 which has a pipe 46 extending therefrom to the liquid inlet side of the heat exchanger 16. A pipe 48 extends from the outlet of the liquid side of the heat exchanger 16 which by means of a Y-connection 50 communicates with two branch conduits 52 and 54 extending respectively to the opposite sides of the pumps 32 and 34. The circuit is completed by pipes 56 and 58 connected respectively to the outlet of the opposite sides of pumps 32 and 34 and the cooled liquid reservoir 22 and heated liquid reservoir 24 respectively. As shown, an overflow pipe 59 is connected between the reservoirs.

The cooling unit 28 is of conventional nature and is adapted to maintain the liquid in the reservoir 22 at a substantially constant temperature as, for example, 30° C. Likewise, the heating unit 30 is of conventional construction and is adapted to maintain the liquid within the heated liquid reservoir 24 at a substantially constant temperature as, for example, 45° C. Pump 32, when operated, serves to meter from the reservoir 22 through pipe 36 an amount of liquid which is equal to the amount of liquid returned through pipe 56. In a similar manner, pump 34 when operated serves to meter an amount of flow from the reservoir 24 which is always equal to the amount returned through return pipe 58. A control, schematically indicated at 60, for varying the rate of movement of the pumps 32 and 34, e.g. electrical controls for the variable speed electrical motors driving the same which form a part of the pump assemblies schematically illustrated is operable so that the total output of the two pumps is adjusted to and maintained at a substantially constant rate, as for example, approximately 10 liters per minute. The control 60 is also operable to effect a proportional variation in the rate which each of the two pumps assume of this total output from 0–10 to 10–0.

Control of the pump assemblies 32 and 34 is undertaken in accordance with the readout of three temperature recording devices 62, 64 and 66 placed respectively to sense the core temperature of the patient's body, the temperature of the blood leaving the heat exchanger 16 being returned to the patient and the temperature of the liquid entering the heat exchanger. A pressure sensing device 68 is also provided in the liquid inlet line 46. It will be understood that the temperature sensing devices and pressure sensing devices are of any conventional design, preferably of the type providing a remote readout, as schematically indicated by corresponding primed numerals.

For illustrative purposes it is sufficient to note that control 60 can be manually operated to determine the proportion of the total liquid flow through the heat exchanger which is provided by the cooled liquid at 30° C. and the heated liquid at 45° C. Control 60 thus serves to directly vary the liquid temperature sensed by device 66 between the low limit of 30° C. and upper limit of 45° C., which in turn will vary the temperature of the blood sensed by device 64 which in turn will affect the patient's systemic blood temperature and hence the temperature sensed by device 62. It will be understood that while the operation of control 60 is set forth for illustrative purposes as being manual, the control 60 may be rendered automatic and programmable if desired.

Figure 1:
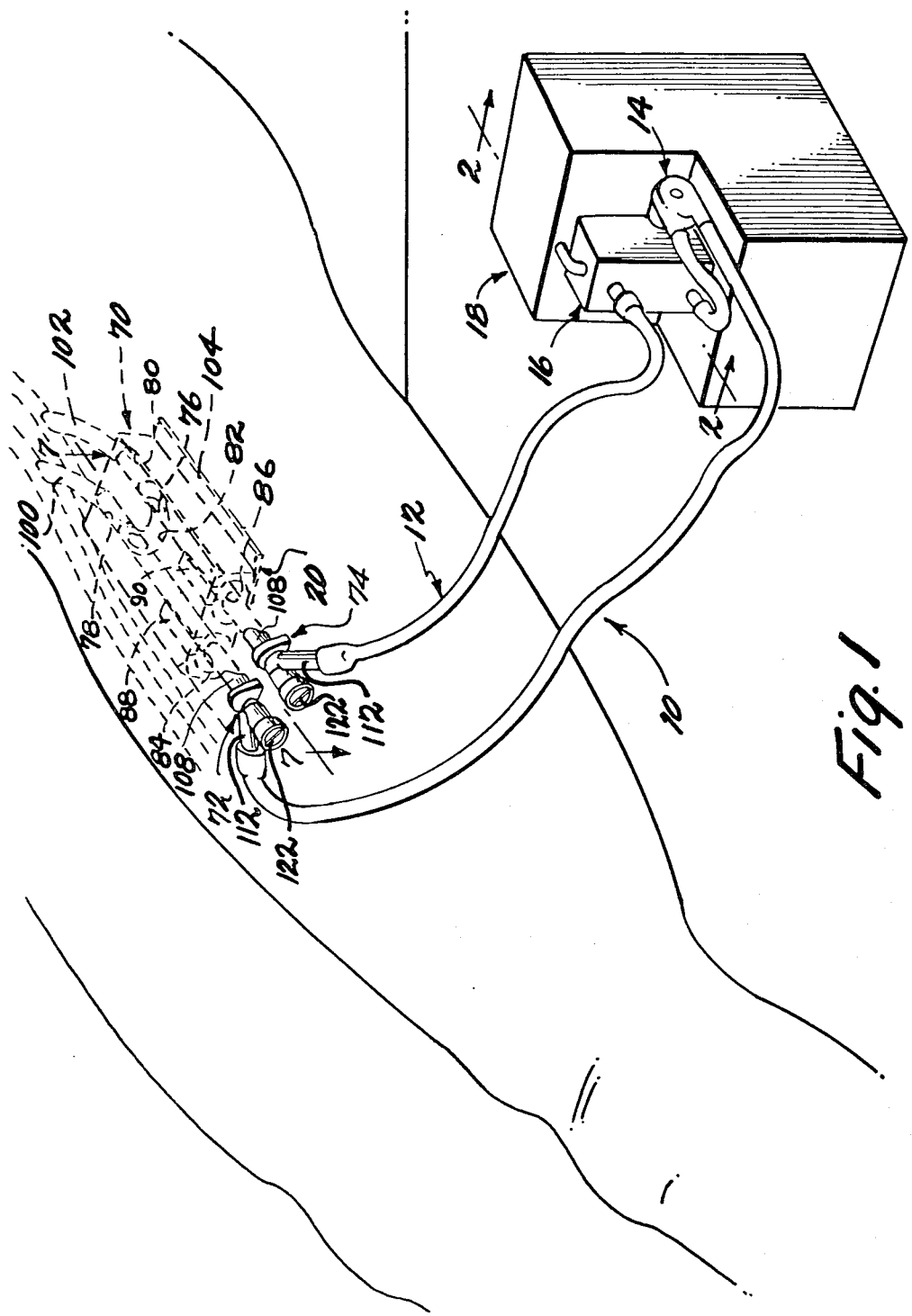
FIG. 1 is a perspective view of a femoral area of a patient showing the apparatus of the present invention applied thereto.

Referring again more particularly to FIG. 1 the communicating means 20 preferably comprises a totally subcutaneous inplant device, generally indicated at 70, which serves as the means communicating with the patient's bloodstream and a pair of percutaneous cannula assemblies, generally indicated at 72 and 74, which serve as the means for operatively communicating the implant device 70 with tubing 12 defining the extracorporeal flow path. As best shown in FIG. 1, the implant device includes a body 76 of elastomeric material such as Silastic ®, molded so as to provide an arterial passage 78, a spaced venous passage 80 and a by-pass conduit 82 connected between the inner end of the passage 78 and the inner end of the passage 80. As best shown in FIG. 1, the passages 78 and 80, together with the by-pass conduit 82, are of generally U-shaped configuration.

Each of the passages 78 and 80 has a peripheral cross-sectional configuration which is elongated in one direction; namely the direction in which they are spaced apart, with sharp points defining opposite ends in the direction of elongation. The preferred configuration shown is further characterized by a pair of convexly curved lines extending between the sharp points, the distance between the central portions of the convex lines being approximately one-half the distance between the two end points. While the by-pass conduit may be of other cross-sectional configuration, as shown, it too is of similar cross-sectional configuration. This preferred cross-sectional configuration for the passages 78 and 80 is provided for the purpose of cooperatively receiving the correspondingly shaped exterior peripheries of the cannula assemblies 72 and 74, which assemblies are so shaped for the purpose of cooperating with a pair of slits 84 and 86 formed in the body 76 in operative association with the passages 78 and 80 respectively.

As shown, each slit 84 and 86 extends from a position exterior of the body 76 to a position of communication with the inner end of the associated passage 78 or 80. The width of each slit is generally equal to the distance between the end points of the associated passage and is oriented in its closed condition, as best shown in FIG. 1, in longitudinal alignment with a plane passing between the end points of the associated passage.

In a closed condition wherein the cannula assemblies are removed, the two planar interior surfaces of the body 76 which define the respective slit 84 or 86 are resiliently urged into engagement by the elastomeric characteristics of the body material. The engagement of the surfaces serves to exclude any spaces which could contain fluid such as blood between the two positions of extent of the slit, as aforesaid.

The resiliency of the elastomeric material of the body 76 also permits each slit 84 and 86 to be moved by its respective cannula assembly 72 and 74 with a trocar (not shown) mounted therein with a protruding sharp end into an open condition where the planar body surfaces defining the slit are spread arcuately so that the profile thereof coincides with the peripheral configuration of the associated passage 78 or 80.

To aid the entry and insertion of each cannula-trocar assembly through its associated slit, there is molded in embedded relation within the body 76 a pair of metallic guide structures 88 and 90. Each guide structure is preferably made of medically acceptable interior use metal, such as stainless steel (e.g. Vitallium Metal manufactured by Howmedica). The implant device 70 also includes a pair of tubes 100 and 102 made of vascular prosthesis material. A preferred vascular prosthesis material is woven Dacron ® marketed commercially by Meadox Medicals although any other acceptable vascular prosthesis material may be utilized. As best shown in FIG. 1, the tube 100 has one end thereof fixed in communicating relation with the outer end portion of the arterial passage 78, as by being molded in embedded relation. The opposite end of the tube 100 is adapted to be connected, as by suture, to a surgical opening formed in the side wall of a femoral artery so that the interior of the tube 100 is in communicating relation with the interior of the femoral artery. In a like manner, one end of the tube 102 is embedded in communicating relation with the outer end portion of the venous passage 80 and its opposite end is adapted to be sutured to a surgical side wall opening in the associated femoral vein so that its interior is in communicating relation with the femoral vein.

The implant device 70 also includes a layer of fabric 104 which is fixed to the inner side wall of the elastomeric body as by Silastic ® glue or the like. The fabric 104 includes marginal portions extending laterally outwardly from the operative inner side wall of the body 76 to which it is fixed. The fabric layer 104 and particularly the marginal portions thereof provide for initial fixation by suture of the body 76 during implant and for subsequent semipermanent fixation by tissue ingrowth. A preferred fabric material in Dacron ® double velour which is marketed commercially by Meadox Medicals.

For identification purposes directly from the implant device itself, radiopaque identification (not shown) is provided on the operative outer side wall of the elastomeric body 76. Such identification insures that the proper cooperating cannula assemblies 72 and 74 will always be used since such assemblies can be ascertained from the implant itself after total implantation has been effected through X-ray identification.

It will be understood that since the assemblies 72 and 74 are left and right hand mirror images of one another, a description of one of the assemblies will suffice to give an understanding of both. Each assembly includes a percutaneous cannula 106 comprising a tubular body which includes a straight section defining the subcutaneous end portion of the cannula and an angular section 112 which, together with an adjacent part of the straight section, defines the extracorporeal end portion of the cannula. The cannula 106 is preferably molded of radiopaque plastic material having sufficient rigidity to prevent interior collapse when in operative position within the implant device 70. Thermoset plastics are preferred although thermoplastic materials with sufficient functional rigidity and heat stability for sterilization can be used. An exemplary material is ethylene-propylene-terpolymer (e.g. where the third monomer is nonbornadiene) impregnated with a radiopaque material such as barium sulfate.

As shown, the entire straight section of the cannula 106 has its exterior periphery formed with a cross-sectional configuration which conforms with and engages within the interior periphery of the body 76 defining the artery passage 78 or venous passage 80. Such configuration, however, is required only in the extent of the subcutaneous end portion which is disposed within the passage and associated slit of the implant body during operation.

The cannula 106 includes an interior passage which extends through the angular section 112 into the straight section 110 and out of the extremity thereof. In order to maximize the interior passage cross-sectional area for an optimum exterior cross-sectional size, the cross-sectional configuration of the interior passage at least in the straight section, conforms to the exterior cross-sectional configuration.

In this regard it will be noted that the cooperating trocar (not shown) preferably consists essentially of a molded body of plastic material, similar to the plastic material of the cannula 106, which provides a blade part and a handle part. The blade part is of a longitudinal extent generally equal to the longitudinal extent of the straight section of the cannula 106. The main extent of the blade part has an exterior peripheral cross-sectional configuration conforming with the interior cross-sectional configuration of the portion of the interior passage extending through the straight cannula section. The blade part includes a sharpened tip portion which tapers gradually in cross-sectional configuration outwardly from the aforesaid configuration to a point.

It will be noted that the extracorporeal end of the straight section of each cannula 106 is closed as by a diaphragm or plug of elastomeric material 122 which preferably is preslit (although may be imperforate) to permit the passage of the trocar, pointed end first, therethrough.

The exterior periphery of the outer end of the angular section 112 is provided with gripping flanges operable to effect a fluid-tight connection with the interior of the tubing 12. When the trocar is withdrawn as shown, the elastomeric plug slit, which has expanded to receive the trocar, contracts to close the end of the straight section of the cannula and insure that all of the blood will flow outwardly through the angular section 112 and into the tubing 12.

Formed on the exterior periphery of the straight section of the cannula is an annular shoulder which forms a stop surface facing in a direction toward the open extremity of the straight cannula section operable to engage the guide part of the implant device when the cannula is in its fully inserted operative position, as shown in FIG. 1. The straight cannula section is formed with an opening which extends inwardly from one exterior end point into communication with the interior passage at a position to register with the by-pass conduit 82 of the implant body 76 when the cannula is fully inserted, as aforesaid.

A preferred procedure is to coat all of the blood contacting surfaces of the cannulas 106, tubing 12 and elastomeric body 76 (passages 78 and 80, conduit 82 and slits 84 and 86) with an anticoagulant coating. A suitable coating material for this purpose is marketed commercially under the generic tradename TDMAC.

The manner in which the device 70 is surgically implanted is in accordance with usual implant procedures well known to those skilled in the art. For present purposes suffice it to say that the elastomeric body 76 is implanted in an anterior femoral region spaced downwardly from the position of bending at the hip approximately the distance of the width of a normal-sized palm (approximately 4") as is clearly shown in FIG. 1. The large area faces of the body 76 are preferably disposed parallel with the skin with the face having the fabric 104 fixed thereto innermost. The arterial and venous tubes 100 and 102 extend upwardly and free ends are tapered and sutured to surgical openings in the side walls of the femoral artery and vein respectively so as to extend therefrom at an angle of approximately 45° C. This procedure is accomplished in accordance with usual practices relating to the use of vascular prosthesis material.

The marginal edge portions of the fabric 104 is sutured to the adjacent tissue to provide initial body 76 fixation, as aforesaid. All of the exterior surfaces of the implant device 76 are contacted with tissue (with fat).

As previously indicated, it is possible to use known shunt devices (e.g. U.S. Pat. No. 3,713,441) in lieu of the device 70 so long as they provide the necessary capacity which is ordinarily not the case without modification.

The manner in which each cannula assembly 72 or 74 is inserted into cooperating relation to the implanted device 70 should be apparent from the above. It is of significance to note the advantages of the utilization of a main implant body 76 which provides increase palpation facility during cannulation. Moreover, cannulation is effected in a straight line relationship resulting in a straight line percutaneous communication with the extracorporeal flow path. The preferred cross-sectional configuration of the cannula enables simple but effective alignment to be accomplished during insertion. Such cross-sectional configuration also provides optimal cooperation with the slits 84 and 86 of the elastomeric body 76 both in expanding the slits during insertion and in contracting the peripheral portion of the cannula extending therethrough to insure a good fluid-tight connection. The extension of this cannular cross-sectional configuration with the elastomeric body passages 78 and 80 also insures non-distortion of these passages and a ful flow area of 4 mm or larger.

It will be understood that one the inlet and outlet ends of the tubing 12 are connected over the flanges of the cannula of the assemblies 72 and 74 and the associated trocars of the assemblies are withdrawn, pump 14 can be started to commence the flow of blood along the extracorporeal flow path at the approximate 1 liter per minute as aforesaid and through the temperature control zone thereof. Initially, control 60 is set to pass 100% 45° C. water through the heat exchanger 16. During this initial treatment phase withdrawn blood temperatures measured at 62 will show a gradual increase from the initial normal reading of approximately 37° C.

Figure 3:
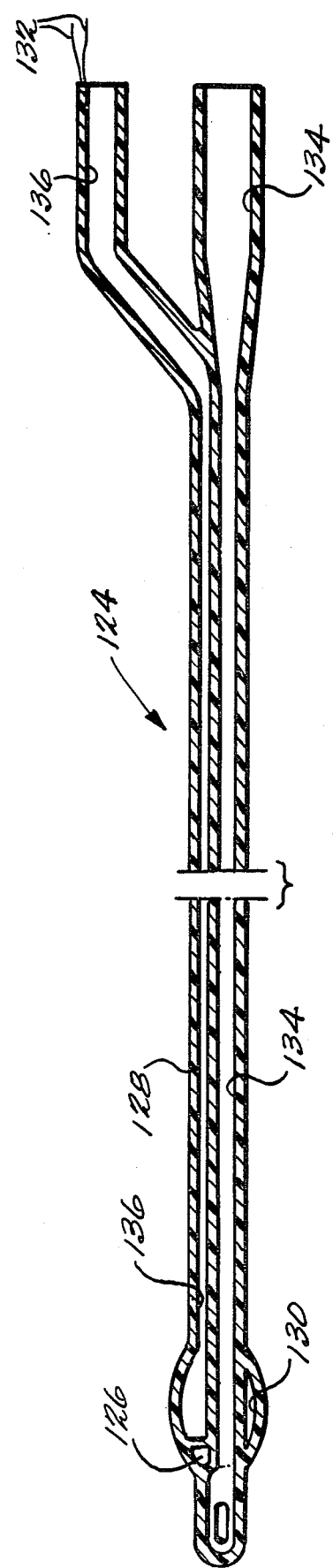
FIG. 3 is an enlarged vertical sectional view of a thermistor-tipped bladder catheter utilized as an improvement in the apparatus shown in FIG. 1 for practicing the improved procedures of the method shown in FIG. 1.

In accordance with the principles of the present invention the improvement thereof consists essentially in utilizing a combined temperature probe and bladder catheter assembly, generally indicated at 124, for accomplishing the aforesaid temperature measurement 62 which corresponds with the patient's body core temperature. As shown, assembly 124 includes a thermistor 126 imbedded in an outer catheter wall 128 in close proximity of a balloon chamber 130 therein. The thermistor includes electrical leads which extend therefrom in imbedded relation along the length of the 128 wall to exit from the opposite end in such a way as not to alter the exterior physical characteristics of the catheter body formed by the outer wall. The external leads for the thermistor are illustrated at 132 in FIG. 3. The catheter itself is of conventional bladder type construction having a side opening conduit 134 for carrying urine from a patient's bladder and a retention balloon conduit 136 which terminates in balloon chamber 130. The assembly 124 is used in a manner similar to a conventional bladder catheter with the thermistor providing a temperature measurement which is routed through instrumentalities interconnected by electrical leads, all of which is in accordance with known technology. It will be understood that the assembly 124 is inserted into operative relation with the patient at the start of the hyperthermic treatment or method to be performed.

Thus, as previously indicated, the temperature measurement provided by the assembly 124 during the initial treatment phase will show a gradual increase from the initial normal reading of approximately 37° C. The capacity and effectiveness of the heat exchanger 16 is such that readings of the returning blood taken at 64 closely approximate the 45° C. maximum water temperature utilized. As the heated blood is returned to the femoral vein through the blood receiving percutaneous cannula 106, venous passage 80 and tube 102, it is distributed systemically which, in turn, has the effect of increasing the total systemic temperature. As the patient's core body temperature increases toward the 41.5° C. level, control 60 must be operated to lower the liquid reading at 66 to a value below 45° C. as, for example, 42.5° C. The liquid temperature level stabilized at 42.5° C., the patient core body temperature readings at 62 by the thermistor 126 of the assembly 124, and returning blood readings will stabilize at a desired level of approximately 41.5° C. and 40.0° C. respectively. This critical phase wherein the patient's systemic temperature is increased and stabilized should, as aforesaid, normally be completed within one hour, although here again, variation because of patient size will occur.

Once temperature stabilization is achieved as aforesaid, treatment is continued for a time period effective for the particular cancer which the patient has. A preferred minimum time for all types including simple carcinomas in six hours although treatment times of 20 hours and longer will be required for more complex cancer situations.

Preferably, a third phase of the present method involves utilizing the continued blood flow through the temperature control zone of the extracorporeal flow path to reduce the blood temperature to normal and, hence, the patient's systemic temperature to normal. This phase is initiated by turning control 60 to pass predominantly 30° C. water through the heat exchanger 16. This has the effect of substantially lowering the readings of the returning blood taken at 64. Again, this cooler blood is distributed systemically, causing the systemic temperature to lower until a normal of 37° C. is reached. The decreasing temperature phase normally will require a time period approximately the same as the initial increasing temperature phase although usually somewhat less.

Preferably, the patient is maintained during treatment in a skin contacting environment approximating that of an intensive care room. While it is within the contemplation of the invention to provide a skin insulating environment and even comparable elevated temperatures to inhaled gases, the intensive care like environment is preferred because the temperature level of the skin and respiratory system does not vary significantly from the induced hyperthermia systemic level and access to the patient is much more readily obtained. Moreover, the application of radiation or chemotherapy treatments can be carried on simultaneously if desired.

It thus will be seen that the objects of the invention have been fully and effectively accomplished. It will be realized, however, that the foregoing preferred specific embodiment has been shown and described for the purpose of illustrating the functional and structural principles of this invention and is subject to change without departure from such principles. Therefore, this invention includes all modifications encompassed within the spirit and scope of the following claims.

What is claimed is:

1. In a process of retarding the growth of cancer cells in a human patient which comprises the steps of establishing a sterile extracorporeal flow path for blood having an inlet, an outlet and a temperature control zone therebetween, establishing communication of the inlet and said extracorporeal flow path with the patient's bloodsream so that blood can be withdrawn and supplied to said extracorporeal flow path without adversely affecting the blood circulation in the areas from which the blood is withdrawn, establishing communication of the outlet of said extracorporeal flow path with the patient's bloodstream so that blood flowing from the extracorporal flow path is returned to the bloodstream in such a way as to be distributed systemically, pumping blood withdrawn from the patient's bloodstream along said extracorporeal flow path through said temperature control zone at a controlled rate of at least approximately 1 liter per minute and returning the same to the patient's bloodstream to be distributed systemically, as aforesaid, controlling the temperature of the blood flowing along said extracorporeal flow path through said temperature control zone for an initial period during which the temperature control zone for an initial period during which the temperature level of the blood within the zone is raised without causing the same to reach localized temperatures in excess of approximately 45° C. so that the systemic distribution of the returned blood gradually increases the patient's core body temperature to a generally stable temperature condition at a level of approximately 41.5° C. but not higher than approximately 42.5° C., and maintaining control of the temperature of the blood flowing along said extracorporeal flow path through said temperature control zone at said generally stable temperature for a second time period sufficient to effect the desired treatment; the improvement of which comprises the steps of:

measuring the patient's core body temperature in the patient's bladder and utilizing the measured bladder temperature in controlling the temperature of the blood flowing along said extracorporeal flow path.

2. In a method of treating cancer in which systemic hyperthermia is induced with a temperature accuracy of from 0.1° C. to 0.2° C. the improvement which comprises measuring the induced systemic hyperthemia in the patient's bladder and controlling the induced hyperthermia in accordance with the bladder temperature measured.

3. In an apparatus for hyperthermic treatment of a human patient for the purpose of retarding the growth of cancer cells in the patient comprising means defining a sterile extracorporeal flow path for blood having an inlet, an outlet and a temperature control zone therebetween, means for establishing communication of the inlet of said extracorporeal flow path with the patient's bloodstream so that blood can be withdrawn and supplied to said extracorporeal flow path without adversely affecting the blood circulation in the areas from which the blood is withdrawn, means for establishing communication of the outlet of said extracorporeal flow path with the patient's bloodstream so that blood flowing from the extracorporeal flow path is returned to the bloodstream in such a way as to be distributed systemically, means for pumping blood withdrawn from the patient's bloodstream along said extracorporeal flow path through said temperature control zone at a controlled rate of at least approximately 1 liter per minute and returning the same to the patient's bloodstream to be distributed systemically, as aforesaid, and means for controlling the temperature of the blood flowing along said extracorporeal flow path through said temperature control zone for an initial period during which the temperature level of the blood within the zone is raised without causing the same to reach localized temperatures in excess of approximately 45° C. so that the systemic distribution of the body temperature to a generally stable temperature condition at a level of approximately 41.5° C. but not higher than approximately 42.5° C., and for maintaining control of the temperature of the blood flowing along said extracorporeal flow path through said temperature control zone at said generally stable temperature condition for a second time period sufficient to effect the desired treatment; the improvement which comprises said blood temperature controlling means including a bladder catheter having temperature sensing means embedded in the tip portion thereof, said blood temperature controlling means being operated in accordance with the temperature sensed by said temperature sensing means.

4. The improvement as defined in claim 3 wherein said temperature sensing means comprises a thermister.

* * * * *